(12) United States Patent
Fiorello

(10) Patent No.: US 7,785,541 B1
(45) Date of Patent: Aug. 31, 2010

(54) LASER TARGETED REMOTE CONTROLLED BEE NEST DESTROYER

(76) Inventor: David Fiorello, 2030 Bellmore Ave., North Merrick, NY (US) 11566

( * ) Notice: Subject to any disclaimer, the term of this patent is extended or adjusted under 35 U.S.C. 154(b) by 419 days.

(21) Appl. No.: 12/029,416

(22) Filed: Feb. 11, 2008

(51) Int. Cl.
- *B65D 83/14* (2006.01)
- *B65D 83/16* (2006.01)
- *B65D 83/24* (2006.01)

(52) U.S. Cl. ........................ 422/124; 422/123; 422/292; 222/61; 222/646; 222/648; 222/649; 43/125; 43/900

(58) Field of Classification Search ................. 422/123, 422/124, 292; 222/61, 162, 168, 182, 645–649; 239/141, 347; 43/125, 900
See application file for complete search history.

(56) References Cited

U.S. PATENT DOCUMENTS

| | | | | |
|---|---|---|---|---|
| 3,589,563 A | * | 6/1971 | Carragan et al. | 222/648 |
| 4,235,373 A | * | 11/1980 | Clark | 239/34 |
| 4,971,257 A | * | 11/1990 | Birge | 239/708 |
| 2006/0216214 A1 | * | 9/2006 | Brown et al. | 422/124 |

* cited by examiner

*Primary Examiner*—Walter D Griffin
*Assistant Examiner*—Christopher K VanDeusen
(74) *Attorney, Agent, or Firm*—Michael I. Kroll

(57) ABSTRACT

A mount for aiming and firing an aerosol spray can having housing with legs extending from a housing point creating a central axis whereby the housing and aerosol can freely rotate 360 degrees serving to stir the can contents and having rotative fasteners for fixing the angle of the housing and therefore spray path to a desired target and an adjustable laser for targeting and calibrating the device, with an access door and locking member for securing an aerosol spray can therein, whereby when actuated via remote control, operates to turn a cam and series of linkages in a manner whereby a pushrod is driven downwards to discharge the held aerosol can at an interval relative to the cams speed setting.

17 Claims, 18 Drawing Sheets

ALIGNMENT TEST

```
                    PROCEDURE FOR SIGHTING IN
                         THE LASER BEAM

S1 ──   LOAD AEROSOL CAN INTO REMOTE
             CONTROLLED NEST DESTROYER

S2 ──   ROTATE CAN SUCH THAT NOZZLE IS
                    FACING OUTWARD

S3 ──   ACTIVATE NOZZLE TO DETERMINE
                   SPRAY DIRECTION

S4 ──         TURN ON LASER BEAM

S5 ──   USING MULTI-AXIS POSITIONING
            KNOB, FINE TUNE BEAM DIRECTION
                 TO COINCIDE WITH SPRAY

S6 ──   LOCK MULTI-AXIS POSITIONING KNOB
              TO STABILIZE LASER POSITION
```

FIG. 15

PROCEDURE FOR SIGHTING IN THE TARGET — 10

- S1: LOAD AEROSOL CAN AND SIGHT IN LASER
- S2: IDENTIFY PROPER DISTANCE BETWEEN AEROSOL NOZZLE AND TARGET (AEROSOL INSTRUCTIONS)
- S3: POSITION BASE UNIT WITHIN IDENTIFIED DISTANCE WITH FRONT POSITIONED TOWARD TARGET
- S4: TURN ON LASER BEAM
- S5: ALIGN LASER BEAM WITH TARGET VERTICALLY BY ROTATING DOCKING PLATFORM ABOUT THE BASE OF THE UNIT
- S6: TIGHTEN SCREW TO SECURE DOCKING PLATFORM IN VERTICAL POSITION
- S7: ALIGN LASER BEAM WITH TARGET BY MANUALLY ROTATING BASE OF REMOTE CONTROLLED NEST DESTROYER

FIG. 16

LASER TARGETED REMOTE CONTROLLED BEE NEST DESTROYER

BACKGROUND OF THE INVENTION

Field of the Invention

The present invention relates generally to aerosol can dispensers and, more specifically, to a dispenser for an aerosol can having a housing for releasably retaining an aerosol can with at least one flexure support extending from the housing to a platform whereby the housing can be tilted in a desired vertical direction so that an amount of aerosol can be discharged in a predetermined direction.

Contained within the housing is a timer for selecting a time period for cyclically dispensing an amount of aerosol, such as an air freshener.

Also contained within the housing is circuitry responsive to a remote control whereby the can contents can be repeatedly dispensed using said remote.

In addition, the housing has a laser which is gimbaled so that the laser can be aligned with the sprayed content point of impact on a desired target.

In this use the purpose is to ascertain a point of spray impact using the laser without discharging the aerosol. Such a use is beneficial when discharging an insecticide against potentially dangerous insects such as a wasp or bees nest.

In operation, the user approximates the distance to the nest and sets up the device remotely from the nest with a target positioned at the approximated distance and discharges the can while aligning the laser to the point of impact. The device is then moved to the approximated distance from the nest whereupon the housing is tilted by means of rotation until the laser engages the desired point of spray impact thereby enabling the user to move away from the device and discharge the insecticide using the remote control.

The present invention further provides that the housing may be of a color pattern, such as yellow and black, which will draw the insects to attack the spray dispenser.

Furthermore, considering that spray cans can be of various sizes with varying type of discharge buttons, the present invention provides for replaceable actuators extending from the motorized discharge switch to the aerosol can discharge button.

The device of the present invention may also be used for periodic discharging of either insecticide or an air fragrance can.

DESCRIPTION OF THE PRIOR ART

There are other spray can dispensers. Typical of these is U.S. Pat. No. 4,248,360 issued to Crump on Feb. 3, 1981.

Another patent was issued to Klein, I et al. on Feb. 9, 1999 as U.S. Pat. No. 5,868,840. Yet another U.S. Pat. No. 6,293,442 was issued to Mollayan on Sep. 25, 2001 and still yet another was issued on Sep. 17, 2002 to Gurule as U.S. Pat. No. 6,450,423.

Another patent application was filed by Bednarz et al. and published on Mar. 27, 2003 as U.S. Patent Application No. 2003/0059523. Yet another U.S. Pat. No. 6,896,192 was issued to Horan et al. on May 24, 2005. Another was issued to Grey et al. on Sep. 26, 2006 as U.S. Pat. No. 7,111,756 and still yet another was issued on Aug. 7, 2007 to Schultz et al. as U.S. Pat. No. 7,252,210.

Another patent application was filed by Ferrari and published on Aug. 3, 1999 as International Patent Application No. WO00/07741 Yet another Korean Patent No. KR20020011100 was issued to Demuth on Feb. 2, 2002. Another was issued to Scholz on Feb. 9, 2005 as European Patent No. EP1504823 and still yet another application was filed by Kuchera and published on Aug. 25, 2005 as International Patent Application No. WO2005076848.

U.S. Pat. No. 4,248,360

Inventor: Robert F. Crump

Issued: Feb. 3, 1981

A remote control cap that is adapted to snap fit onto a spray can's head, the cap being of a unitary or one piece molded plastic structure. The cap includes a lever arm connected to a snap-on collar by inherently resilient leaf springs, the leaf springs normally biasing the lever arm out of contact with the can's valve when the cap is assembled with the can. The cap also includes a pole socket connectable to an extension pole, and the lever arm is connectable to an extension cord at an end remote from the leaf spring end, thereby permitting the can's valve to be operated by depressing the lever arm against the leaf spings' bias from a position remote from the can.

U.S. Pat. No. 5,868,840

Inventor: Richard J. Klein, II et al

Issued: Feb. 9, 1999

A spray gun for applying a liquid spray coating, such as paint, to a surface incorporates a light source and detection system for analyzing the position of the spray gun relative to a worksurface in order to optimize application of the coating to the surface. The light source is preferably in the form of a laser which emits a beam of light toward the worksurface. The laser is interconnected with the housing of the spray gun in a location over the spray gun handle so as not to effect the center of gravity of the spray gun. Optical sensors are mounted to the spray gun housing for receiving light reflected from the worksurface, and the sensors are interconnected with a processor for providing the operator with a real time visual indication as to compliance with predetermined paint application criteria. In addition, information can be stored to memory and downloaded for subsequent analysis.

U.S. Pat. No. 6,293,442

Inventor: Girard D. Mollayan

Issued: Sep. 25, 2001

A timed spray dispenser for distributing a liquid deodorizer from an aerosol spray can, using a finger actuated spray valve, that incorporates a structural housing (22) with a radial cavity (28) of a size to accommodate the spray can. A lever arm (42) pivots on the housing and encompasses the spray valve on one end. An eccentric cam (56) engages the other end of the lever arm and raises the arm when the cam is rotated with a motor (62). A timer (68) electrically attached to the motor is employed when specific time duration and frequency is required by the dispenser. Height adjustment of the dispenser is achieved to accommodate various sizes of cans by separating the housing from the base (24) using posts (32) that slide into bores (36) in the housing and securing the adjustment using thumb screws (38). A second embodiment provides height adjustment using a fixed height housing and a sliding shelf (74). A third embodiment adds an enclosure (29) that covers the entire dispenser and an optional remote or manually actuated reset switch (84) to operate the dispenser from the switch or from a remote location.

U.S. Pat. No. 6,450,423

Inventor: Randy F. Gurule

Issued: Sep. 17, 2002

A spray can remote control has a body holding and registering the can at a raised top wall portion, and a control mechanism including an actuator guided parallel to a nozzle axis of movement, a branched flexible lanyard for coupling a pull cord, flexible branches of the lanyard connected through a pair of guide rods to opposite ends of the actuator, whereby downward movement of the coupling produces corresponding downward movement of the guide rods and the actuator member without imparting side force to the nozzle button. Respective helical compression springs on the guide rods upwardly bias the actuator member, and stationary guides below the guide rods prevent side forces on the guide rods. The device also has an adjustable handle member, and a pair of sheaves for offsetting the lanyard to facilitate precise control with minimal frictional drag.

U.S. Patent Application Number 2003/0059523

Inventor: Vincent L. Bednarz

Published: Mar. 27, 2003

A remote control device that provides a wireless connection between the operator and a control console of a material coating spraying system, thereby allowing the operator to select, change, modify and otherwise control a variety of parameters and functions of the spraying operation. The remote capability permits an operator to be stationed at, in or near the spray booth so as to be able to observe the actual spraying operation and transmit instructions to the control console. In one embodiment, a powder spray system includes a spray gun having a pressurized air inlet and a powder inlet, a powder spray booth, a powder supply for feeding powder to the gun, a control console separately located with respect to the booth; the console being operable to control a spraying operation; and a hand-held remote control device for wireless operation of the control console by an operator positioned a distance from the console.

U.S. Pat. No. 6,896,192

Inventor: Nicholas R. Horan

Issued: May 24, 2005

A spray container positioning device for use in positioning a spray container relative to a surface, for optimizing application of liquid contained within the spray container to a surface upon discharge of the liquid through a nozzle member associated with the spray container. The positioning device further includes a light beam positioning arrangement which projects at least one light beam toward the surface, for use in positioning the spray container and the nozzle member relative to the surface. The light beam positioning arrangement includes a light beam generator, such as a laser generator, which directs at least one light beam toward the surface to form a point of light on the surface which provides a visual indication to the user as to the position of the spray container and nozzle relative to the surface. In one form, the positioning device includes a handle arrangement selectively engageable with the spray container, which includes a manually operable trigger mechanism engageable with the nozzle member for actuating the nozzle member. The light beam generator may be interconnected with the trigger mechanism, for operating the light beam generator prior to actuation of the nozzle member, to provide an initial indication of the position of the spray container. In another form, the light beam generator is associated with a mounting device adapted for engagement with a side wall defined by the spray container. The light beam generator directs the at least one light beam toward the surface while the liquid confined within the spray container is directed through the nozzle member toward the surface, to provide a continuing point of reference as to the position of the nozzle member during movement of the spray container relative to the surface.

U.S. Pat. No. 7,111,756

Inventor: Matthew James Grey et al

Issued: Sep. 26, 2006

A dispensing system for controlled, especially remote controlled, dispensing of medicaments is disclosed. The system consists of a dispensing mechanism adapted to receive a sealed or resealable container of material to be dispensed and to validate that it is the correct material, and which includes a mechanical actuation mechanism which, when actuated, causes a measured dose of material to be dispensed from the material container. The mechanical actuation mechanism may be inhibited from operation by a locking mechanism which, when actuated, locks the device against the further dispensing of a dose of material until release in accordance with the desired dispensing programme, e.g. until a certain time period has elapsed, or until the programme permits dispensing to occur on some other basis. The dispensing system may be in two parts, a hand-held hand-actuated dispensing mechanism (1) and a base or docking station (2) into which the hard-held unit may be placed in order to release the locking mechanism. The docking or base station (2) may be triggered to cooperate with a remote overall control system, for example a remote computer, by placing the handheld dispensing mechanism (1) in it.

U.S. Pat. No. 7,252,210

Inventor: Edwin R. Schultz et al

Issued: Aug. 7, 2007

An aerosol spray article is used to hold an aerosol spray container and spray an object with the container's contents from a remote locale. The article comprises a main body having a cord guide, a clip extending from the main body for holding the aerosol spray container, a pole adaptor adjustably mounted to the main body as needed, and a spray lever operably associated with the main body to contact the aerosol spray container's push button valve actuator. It further has a cord which extends from the spray lever, through the cord guide and along the extension pole to the user. The article allows a spray from the container to be emitted directly onto an object by the user standing at a locale remote from the object.

International Patent Application Number
WO00/07741

Inventor: Giovanni Ferrari

Published: Feb. 17, 2000

A remote control device for paint supplying guns for painting systems, whose particularity is the fact that it comprises a main control unit which is suitable to communicate in a wireless manner with a plurality of remote control units (5), each associated with a respective paint supplying gun (1), said remote control units comprising control means and actuation means for regulating the flow-rate of the respective supplying gun and being remotely controlled by the main control unit (2).

Korean Patent Number KR20020011100

Inventor: Russell Stephens Demuth et al

Issued: Feb. 7, 2002

PURPOSE: A robotic machine and operation method thereof is provided to improve response time for changes in powder feed rates. CONSTITUTION: A robotic machine (10) includes a robotic arm (12) with a machine tool (18) mounted thereto. A powder injector (26) is mounted near the tool. A local powder feeder (28) is mounted to the arm and includes a local conduit (30) for supplying powder to the injector, and a load cell for measuring powder weight therein to control feed rate. A remote powder feeder (32) is spaced from the arm, and includes a remote conduit (34) joined to the local feeder for supplying powder thereto. A process computer (36) controls the arm, and two feeders and effects staged delivery of the powder from the remote feeder to the local feeder for improving powder delivery response time.

European Patent Number EP1504823

Inventor: Dr. Thomas Scholtz

Issued: Feb. 2, 2005

The pistol (4) has a high tension electrode (15) to coat the work (11) when the trigger (8) is pressed. The high tension generator (32) is in a control unit (2) connected to an electrical supply (12) and data on indicator panels (20,30) is transmitted to a remote indicator unit (40) by radio (42,44).

International Patent Application Number
WO2005076848

Inventor: Glen Kuchera et al

Issued: Aug. 25, 2005

A remote control system comprising a transmitter, receiver, and antenna are used to control the functions of a paint sprayer. The system may be retrofit in existing paint sprayers or added during manufacturing. In one embodiment, the remote control system allows a user to control the power and pressure of a paint sprayer. The method of installation and transmission is also described. Alliteratively, an add-on unit or digital display may be provided on the remote transmitter.

While these discharge devices may be suitable for the purposes for which they were designed, they would not be as suitable for the purposes of the present invention, as hereinafter described.

SUMMARY OF THE PRESENT INVENTION

A primary object of the present invention is to provide a mount for aiming and firing an aerosol spray can at a target utilizing a remote control from a safe distant location.

Another object of the present invention is to provide a mount for aiming and firing an aerosol spray can utilizing a laser to aim and calibrate the targeting of a spray discharge, Yet another object of the present invention is to provide a mount for aiming and firing an aerosol spray having housing with legs extending from a housing point creating a central axis whereby the housing and aerosol can freely rotate 360 degrees serving to stir the can contents and having rotative fasteners for fixing the angle of the housing and therefore spray path to a desired target.

Still yet another object of the present invention is to provide a mount for aiming and firing an aerosol spray can that has an access door and locking member, has a cavity that may be adjusted for size, and is magnetically binding to hold and accommodate most any size aerosol spray can.

Another object of the present invention is to provide a mount for aiming and firing an aerosol spray can that utilizes a cam, motor, pushrod and plurality of switches to, on remote command rotate to drive the pushrod downward and discharge the held aerosol spray can.

Yet another object of the present invention is to provide a mount for aiming and firing an aerosol spray can that can be calibrated in one location then fired at another from a safe distance via remote controls Still yet another object of the present invention is to provide amount for aiming and firing an aerosol spray can having a plurality of switches and indicators to toggle the various components that make up the present invention.

Additional objects of the present invention will appear as the description proceeds.

The present invention overcomes the shortcomings of the prior art by providing a mount for aiming and firing an aerosol spray can having housing with legs extending from a housing point creating a central axis whereby the housing and aerosol can freely rotate 360 degrees serving to stir the can contents and having rotative fasteners for fixing the angle of the housing and therefore spray path to a desired target with, an adjustable laser for targeting and calibrating the device, with an access door and locking member for securing an aerosol spray can therein, whereby when actuated via remote control, operates to turn a cam and series of linkages in a manner whereby a pushrod is driven downwards to discharge the held aerosol can at an interval relative to the arms speed setting. Additionally the present invention is remote controlled and has a plurality of toggle switches and indicators to inform the user of proper aiming, setting, calibration and deployment of the present invention in the goal of destroying a hive or nest from a safe remote location.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawings in which:

FIG. 15 is a flow chart for sighting the laser setup procedures for the present invention.

FIG. 16 is a flow chart for sighting target procedures for the present invention.

DESCRIPTION OF THE REFERENCED NUMERALS

Figure 1:
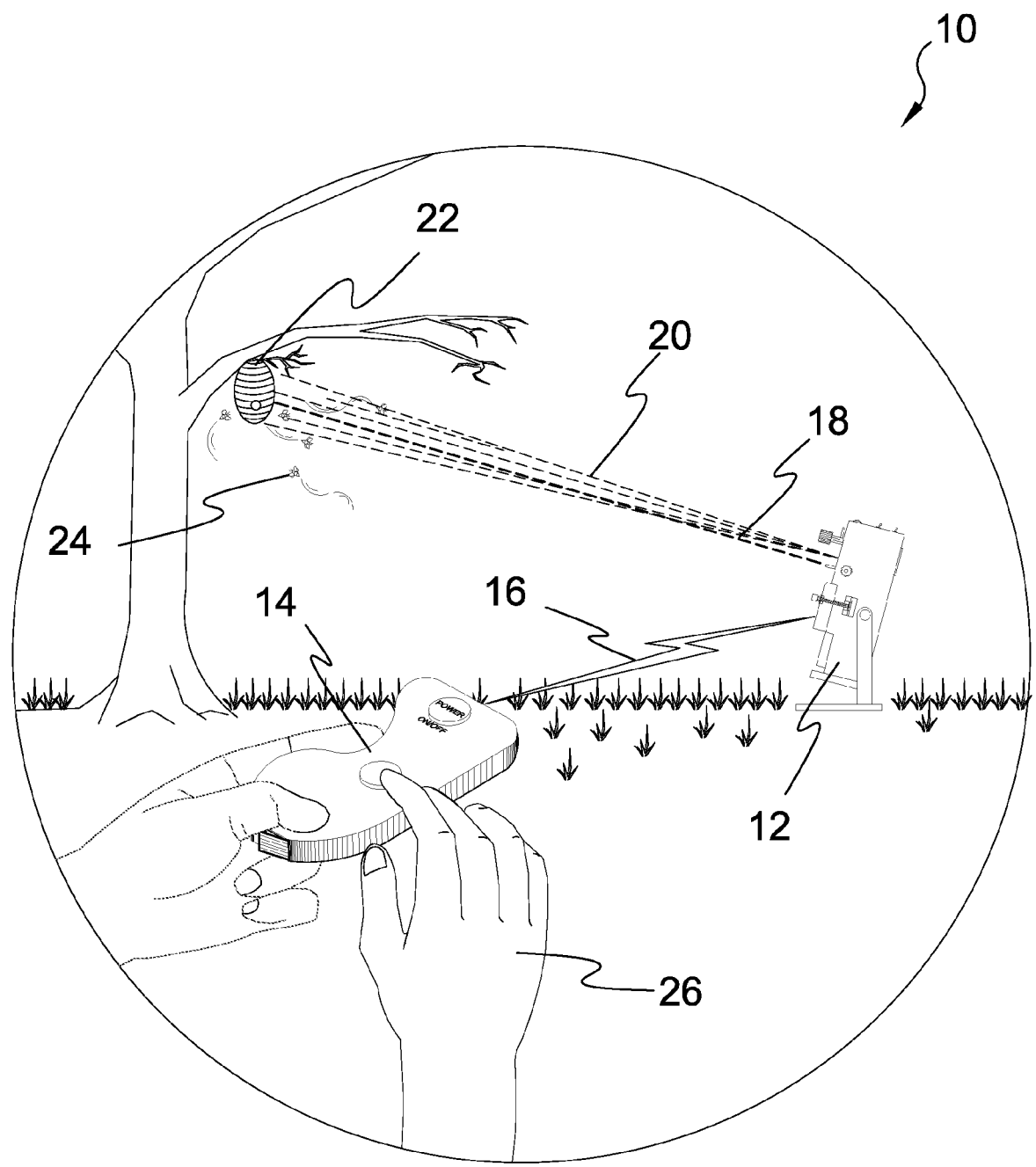
FIG. 1 is an illustrative view of the present invention in use
Figure 2:
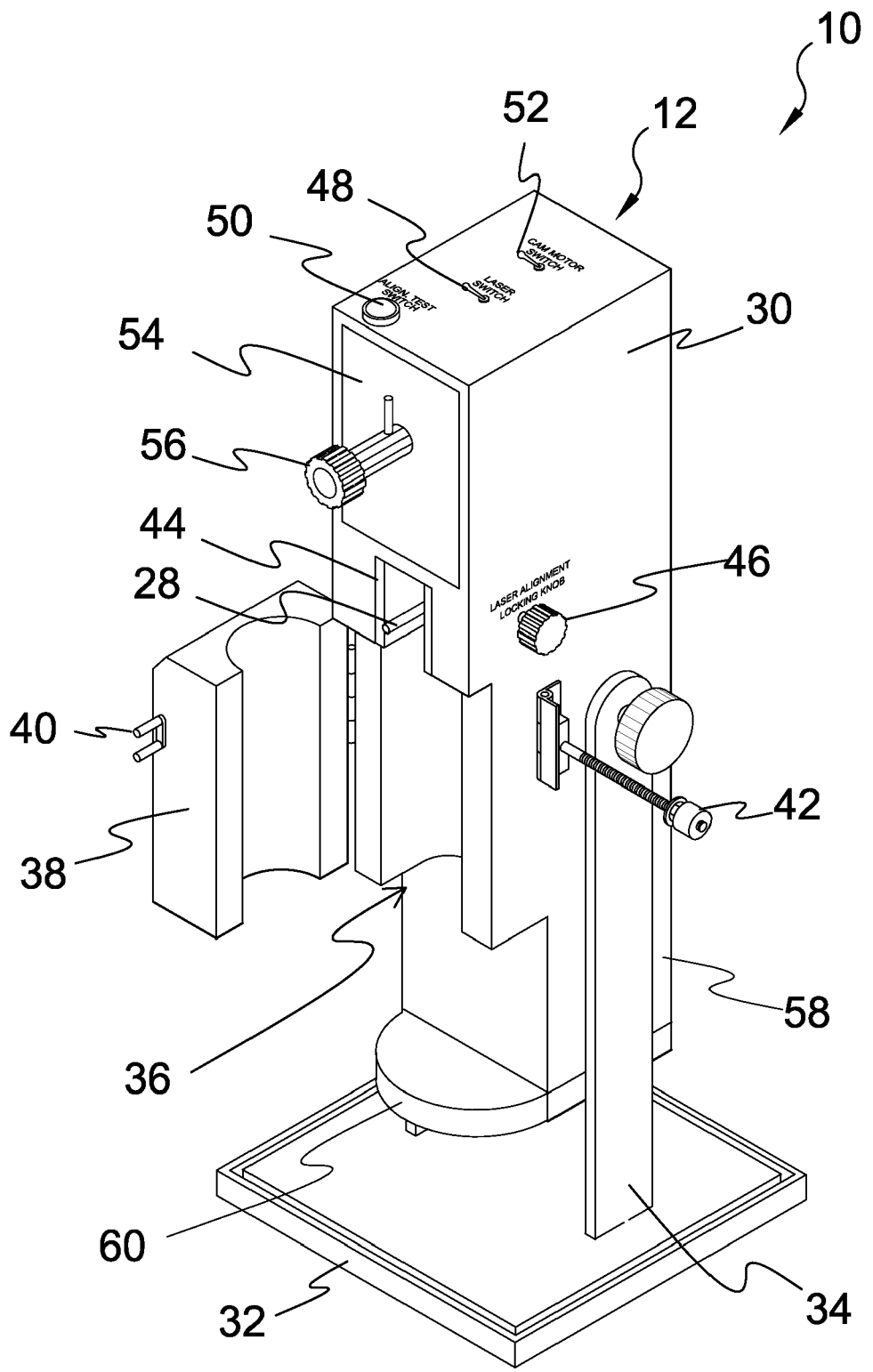
FIG. 2 is a perspective view of the present invention.

Turning now descriptively to the drawings, in which similar reference characters denote similar elements throughout the several views, the figures illustrate the Remote Operated Insecticide and Fragrance Dispensing Apparatus of the present invention. With regard to the reference numerals used, the following numbering is used throughout the various drawing figures.

10 Remote Operated Insecticide and Fragrance Dispensing Apparatus of the present invention
12 dispenser
14 remote control unit
16 remote signal
18 laser target beam
20 insecticide spray
22 bee hive
24 bee
26 user
28 sighting laser pointer
30 housing of 12
32 base of 12
34 360 degree rotating support
36 receiving compartment
38 access door
40 bifurcated latch
42 access door locking member
44 magnet
46 laser alignment locking knob
48 laser switch
50 alignment test button
51 cam motor
52 cam motor switch
54 cam housing
55 cam assembly
56 cam rod
58 storage compartment
60 balancing weight
62 hinge of 42
64 threaded shaft of 42
66 aerosol can
68 spray nozzle of 66
70 lock nut
72 pivot pin
74 rotation alignment locking knob
76 cam
78 microswitch
80 push rod
82 magnetic tip of 80
84 cam plate
86 spray button of 66
88 timer
90 360 degree rotational movement
92 laser adjustment assembly
94 positioning rod
95 holding hub
96 rotative positioning ball
98 storage compartment door
100 rechargeable battery port
102 dispenser carrying cover
104 handle of 102
106 transmitter
108 cam power receiver
110 rechargeable battery

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

FIG. 1 is an illustrative view of the present invention 10 in use. Shown is the remote operated aerosol dispensing device 12 of the present invention 10 in use and depicted with the user 26 operating a remote control unit 14 to send a signal 16 to activate the dispenser 12 for dispensing and operating to aim and shoot an aerosol insecticide 20 spray can, at a targeted nest or hive 22 to exterminate bees 24 and other such hornets from a remote safe location. Additionally, the present invention 10 may be deployed in any location within a spraying range so that a visible laser 18 could be utilized to aim and provide a visual confirmation on a targeted nest or hive 22 of a correct alignment whereby the dispensed spray 20 will reach its target.

FIG. 2 is a perspective view of the dispenser 12 of the present invention 10. Shown is the aerosol can dispensing device 12 having a sighting laser 28 selectively positionable by the user. The dispensing device 12 comprises a housing 30 secured to a base 32 via a 360 degree rotating support 34. An access door 38 is shown open to reveal a aerosol can receiving compartment 36 for receiving and retaining at least one from a plurality of variously sized aerosol cans with a discharge actuator that can be remotely actuated, and magnets 44 that capture and hold to the outer metal rim of the can and act as a positioning point stop. The door 38 is secured with a latch 40 and mating locking member 42. A laser switch 48, alignment test button 50 and laser alignment locking knob 46 serve to target the laser 28 accurately. Also shown is a cam motor switch 52, cam housing 54 and cam rod 56. The housing 30 further includes a storage compartment 58 and balancing weight 60.

Figure 3:
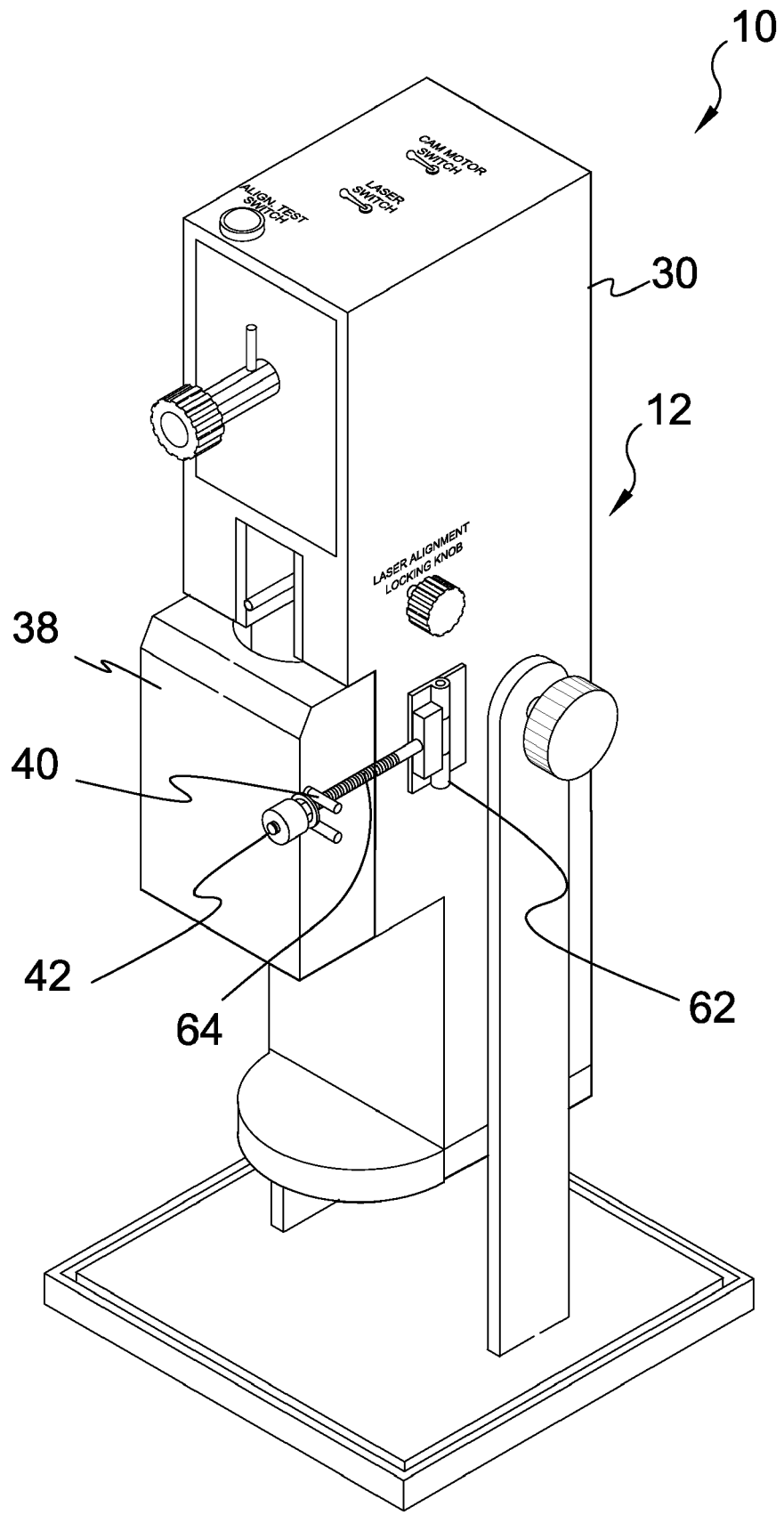
FIG. 3 is a perspective view of the present invention.

FIG. 3 is a perspective view of the dispenser 12 of the present invention 10. Shown is the receiving compartment access door 38 on the housing 30 closed with the access door locking member 42 pivoted on its hinge 62 and tightened against the latch 40 through the use of the threaded shaft 64.

Figure 4:
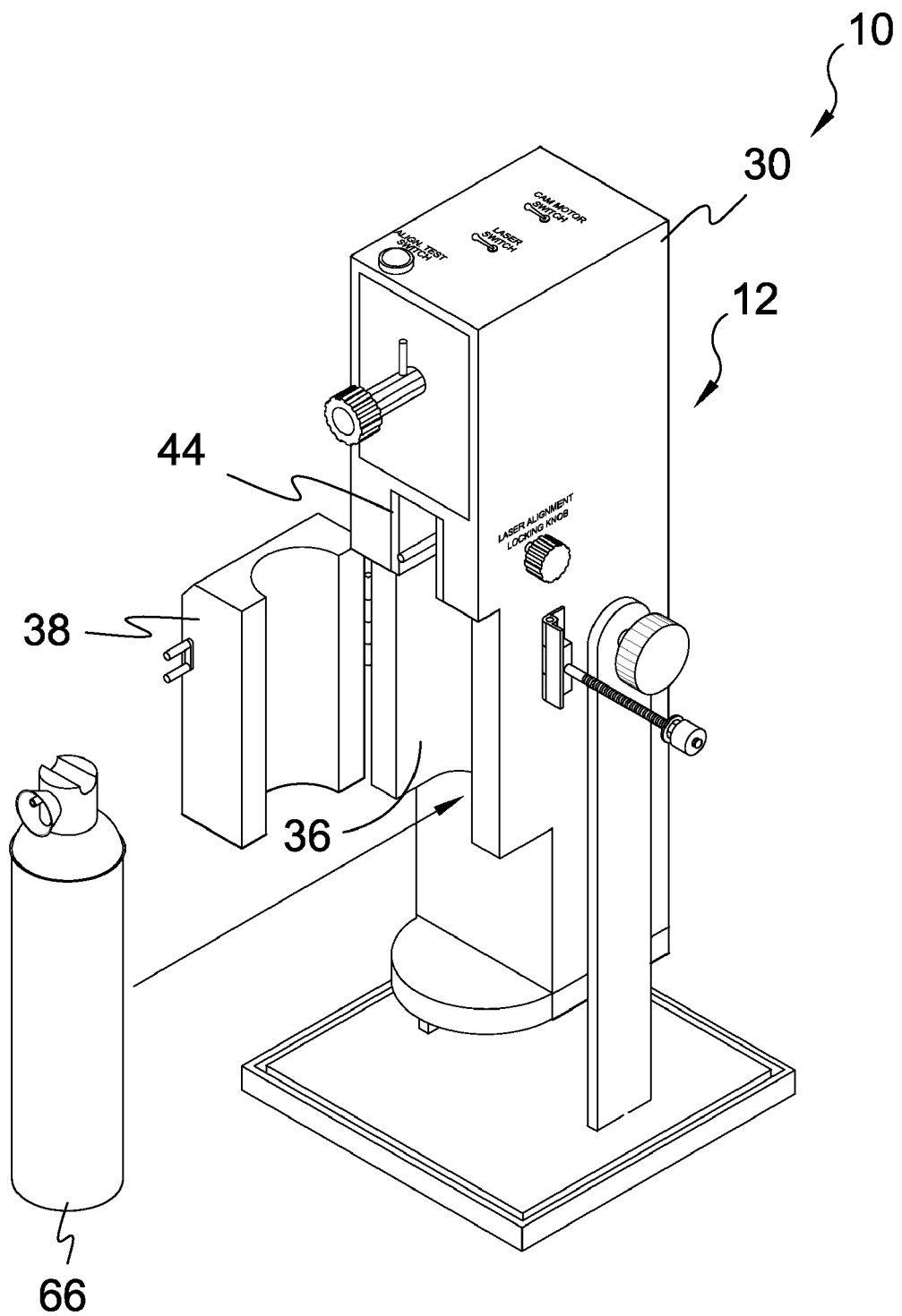
FIG. 4 is a perspective view of the present invention.

FIG. 4 is a perspective view of the dispenser 12 of the present invention 10. Shown is the access door 38 on the housing 30 open and ready to accept an aerosol can 66 into the receiving compartment 36 where it will be retained therein with magnets 44. The receiving compartment 36 and magnets 44 are configured to accept and receive aerosol cans 66 of varying sizes.

Figure 5:
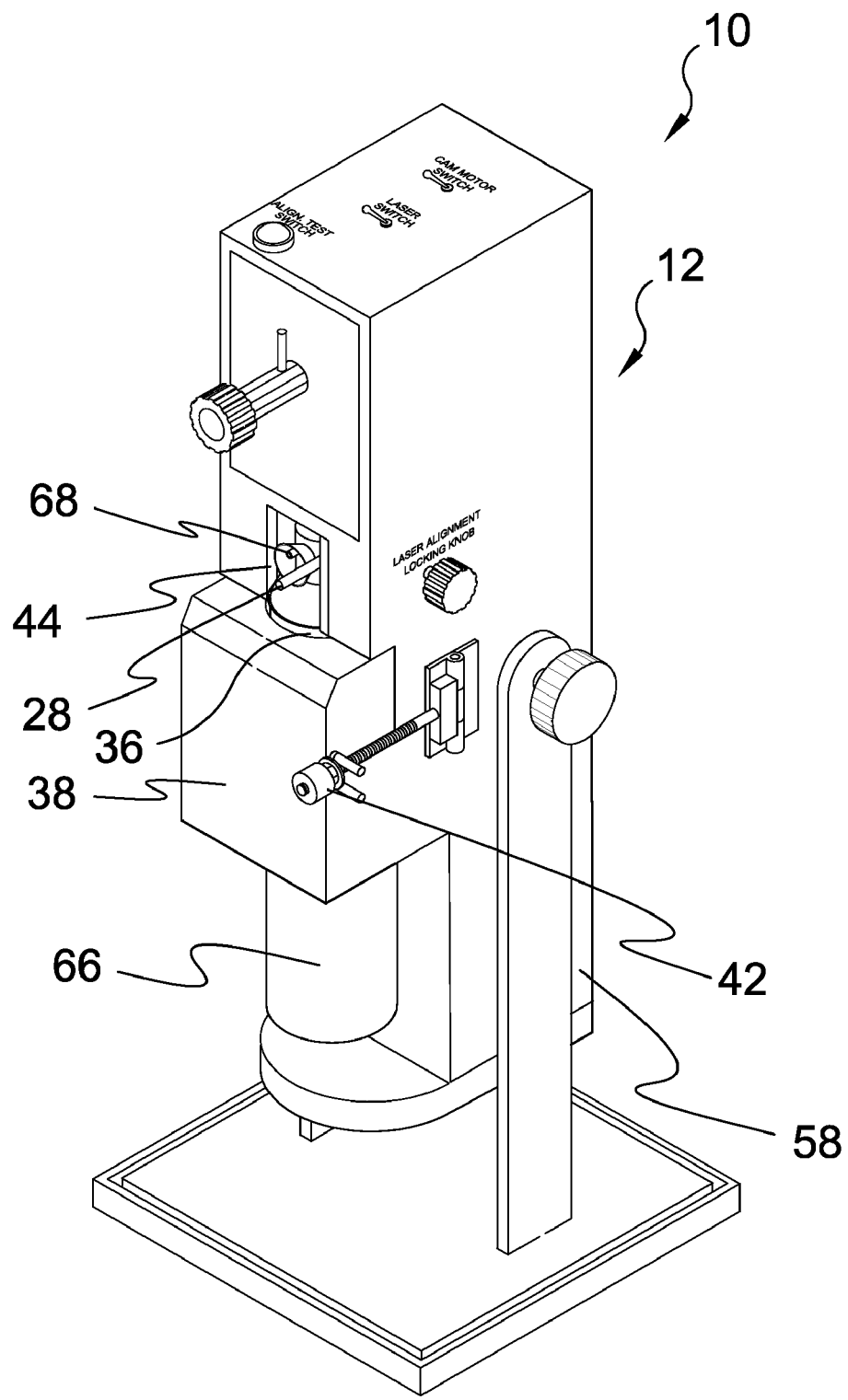
FIG. 5 is a perspective view of the present invention.

FIG. 5 is a perspective view of the dispenser 12 of the present invention 10. Shown is the present invention, an aerosol can dispensing device 12 having a sighting laser 28 adjacent to the spray nozzle 68 selectively positionable by the user. A receiving compartment 36 for receiving and retaining at least one from a plurality of variously sized aerosol cans 66 with a discharge actuator that can be remotely actuated. The access door 38 is closed and secured with the locking member 42. Magnets 44 are provided that capture and hold to the outer metal rim of the can 66 and act as a positioning stop. The device also provides a storage compartment 58, a timer and battery charger.

Figure 6:
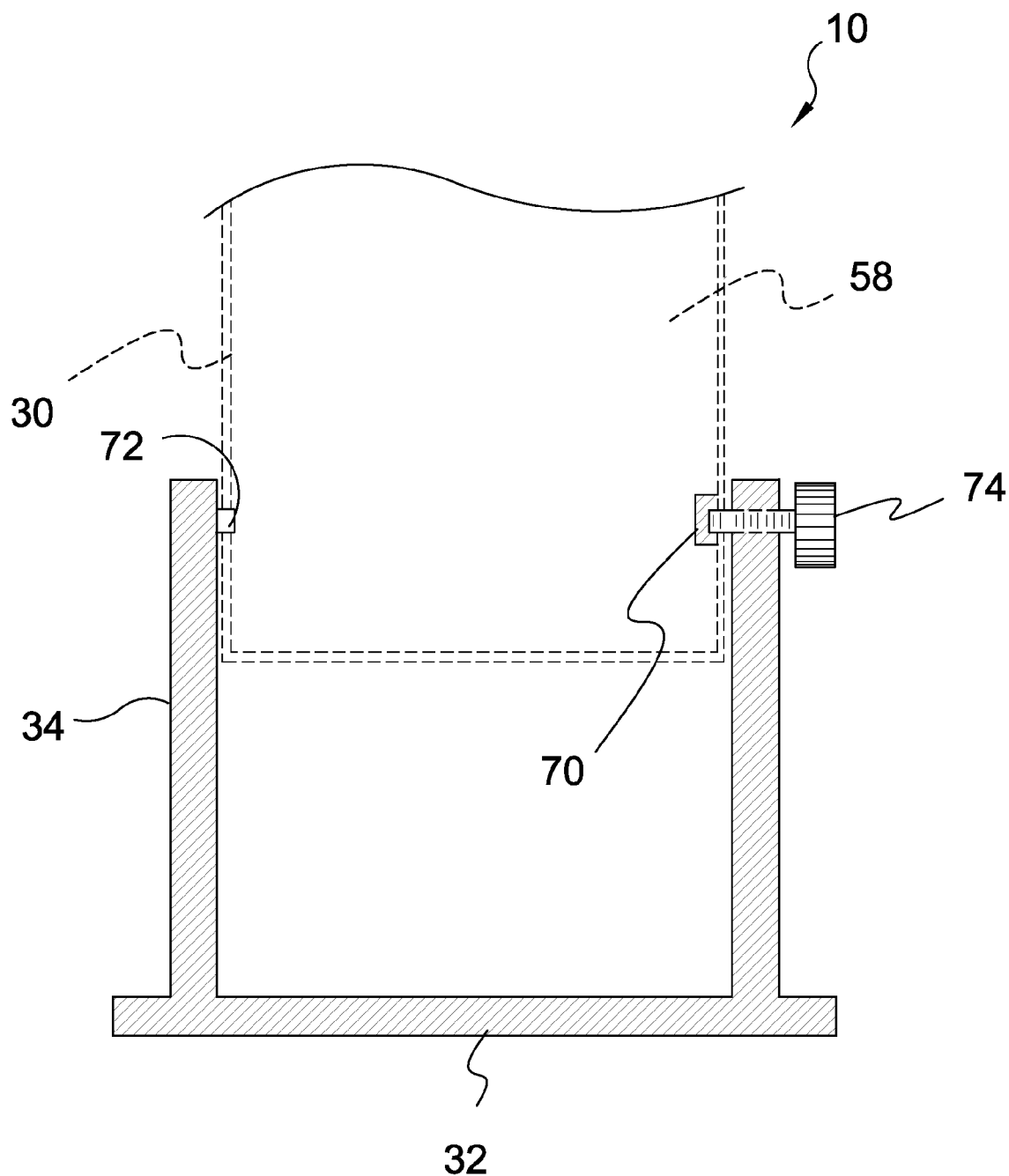
FIG. 6 is a sectional view of the present invention

FIG. 6 is a sectional view of the present invention 10. Shown is the base 32 and rotational support 34 of the present invention 10, allowing the housing 30 to rotate 360 degrees on its axis. This allows the user to target in on a hive at any angle of rotation. The housing 30 is rotatively secured to the rotational support 34 with a pivot pin 72 on one side and the rotation alignment locking knob 74 threaded into a lock nut 70 disposed on the opposing side within the storage compartment 58.

Figure 7:
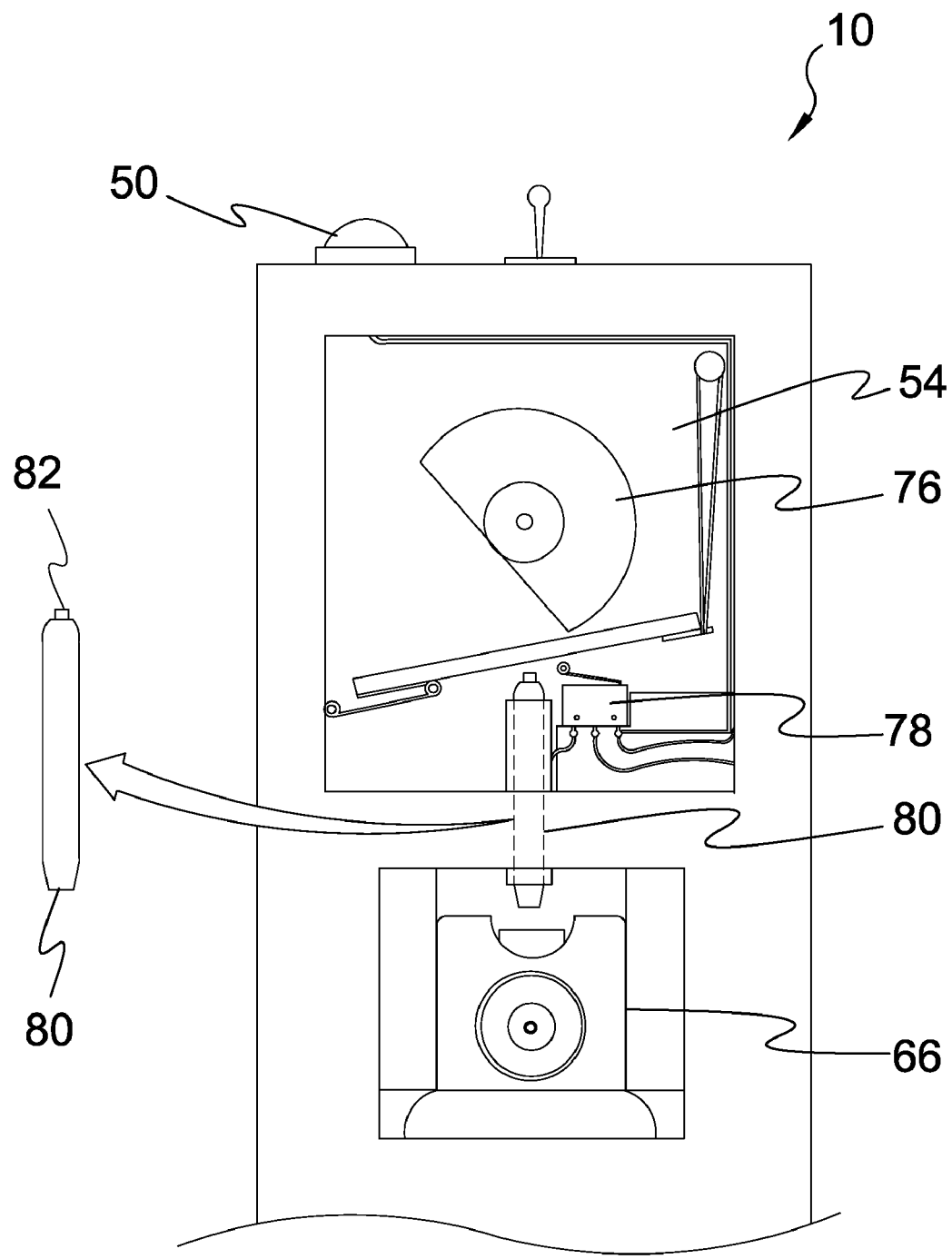
FIG. 7 is a frontal detail view of the present

FIG. 7 is a frontal detail view of the cam housing 54 of the present invention 10. Shown is the present invention 10 comprising a cam housing 54 having a cam 76 (shown in the off position), microswitch 78 and push rod 80 with magnetic tip 82 that work in conjunction to activate the dispersal of spray from an aerosol can 66, using a remote control device. The push rod 80 is provided in various sizes to accommodate the size can 66 being used. An alignment test button 50 is provided for a test spray, after the laser has been locked on to its target.

Figure 8:
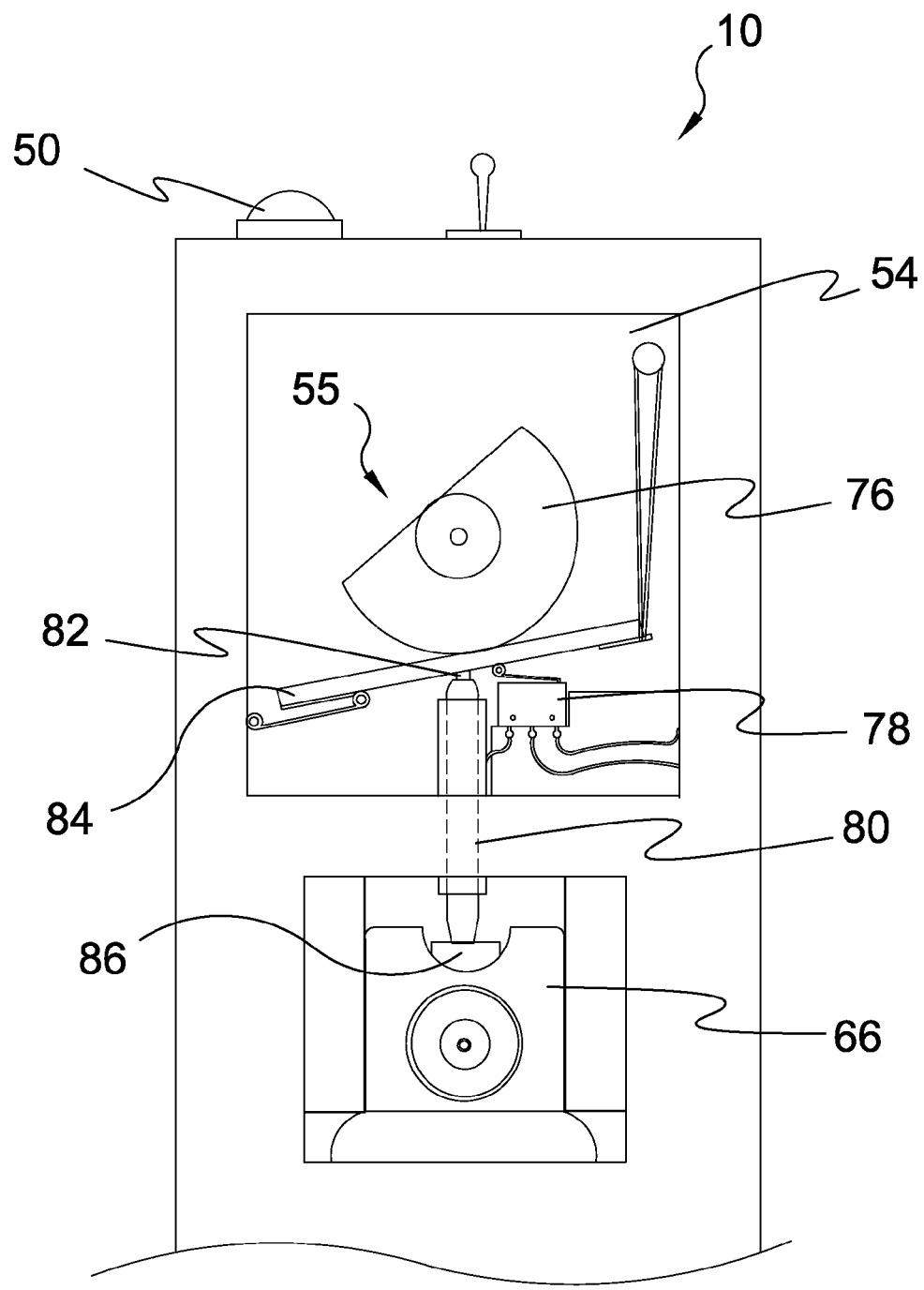
FIG. 8 is a frontal detail view of the present invention in an actuated position.

FIG. 8 is a frontal detail view of the cam assembly 55 in the cam housing 54 of the present invention 10 in an actuated position Shown is the cam 76 rotated into the activated position thereby depressing the cam plate 84 to contact the microswitch 78 and magnetic tip 82 of the push rod 80 to plunge it down against the spray button 86 of the aerosol can 66 to discharge the contents thereof. The push rod 80 is provided in various sizes to accommodate the size can 66 being used. An alignment test button 50 is provided for a test spray, after the laser has been locked on to its target.

Figure 9:
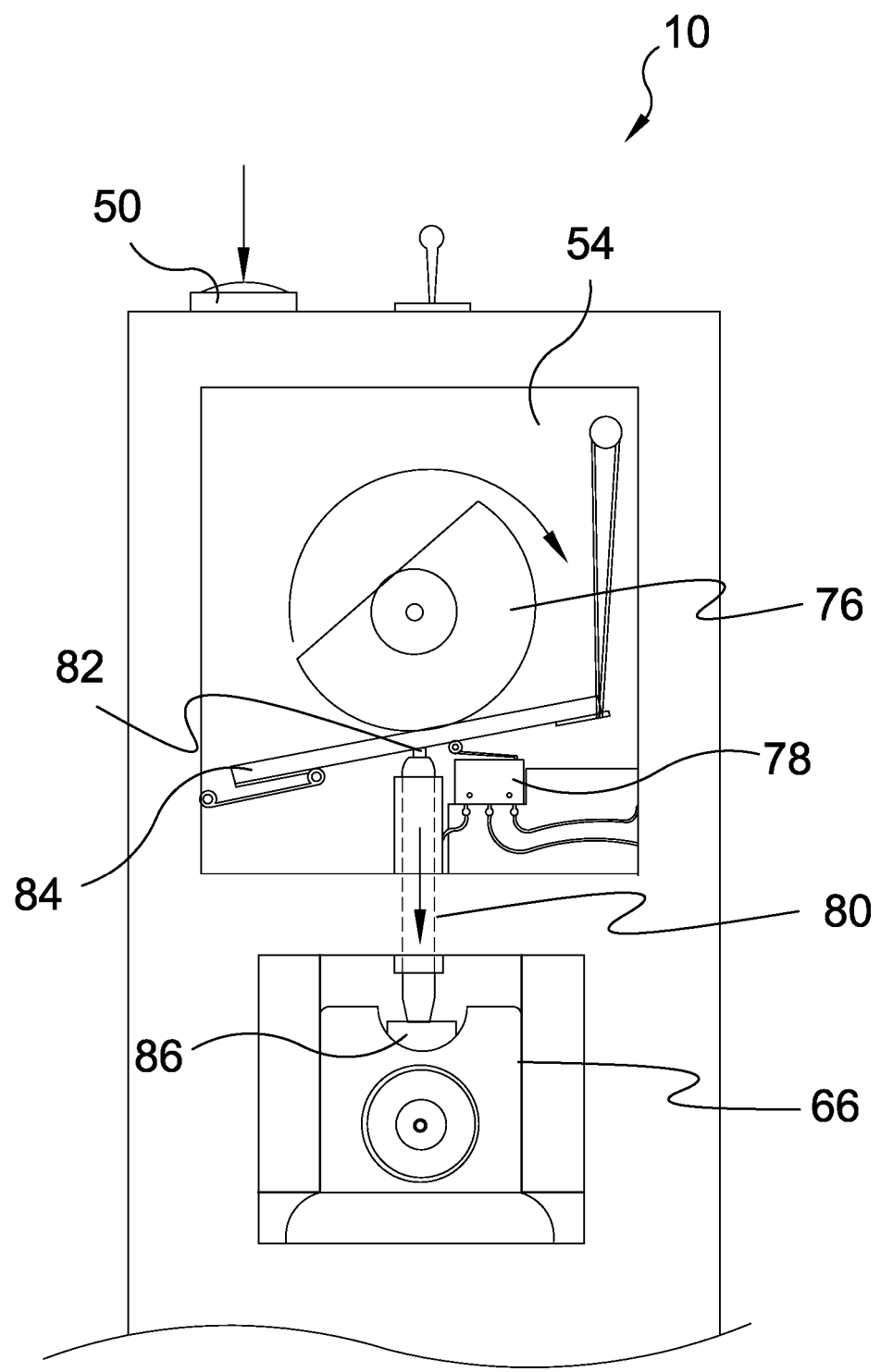
FIG. 9 is a frontal view of the present invention in an actuated position using the alignment test button

FIG. 9 is a frontal view of the cam housing 54 of the present invention 10 in an actuated position using the alignment test button 50. Shown is the cam 76 rotated into the activated position thereby depressing the cam plate 84 to contact the microswitch 78 and magnetic tip 82 of the push rod 80 to plunge it down against the spray button 86 of the aerosol can 66.

Figure 10:
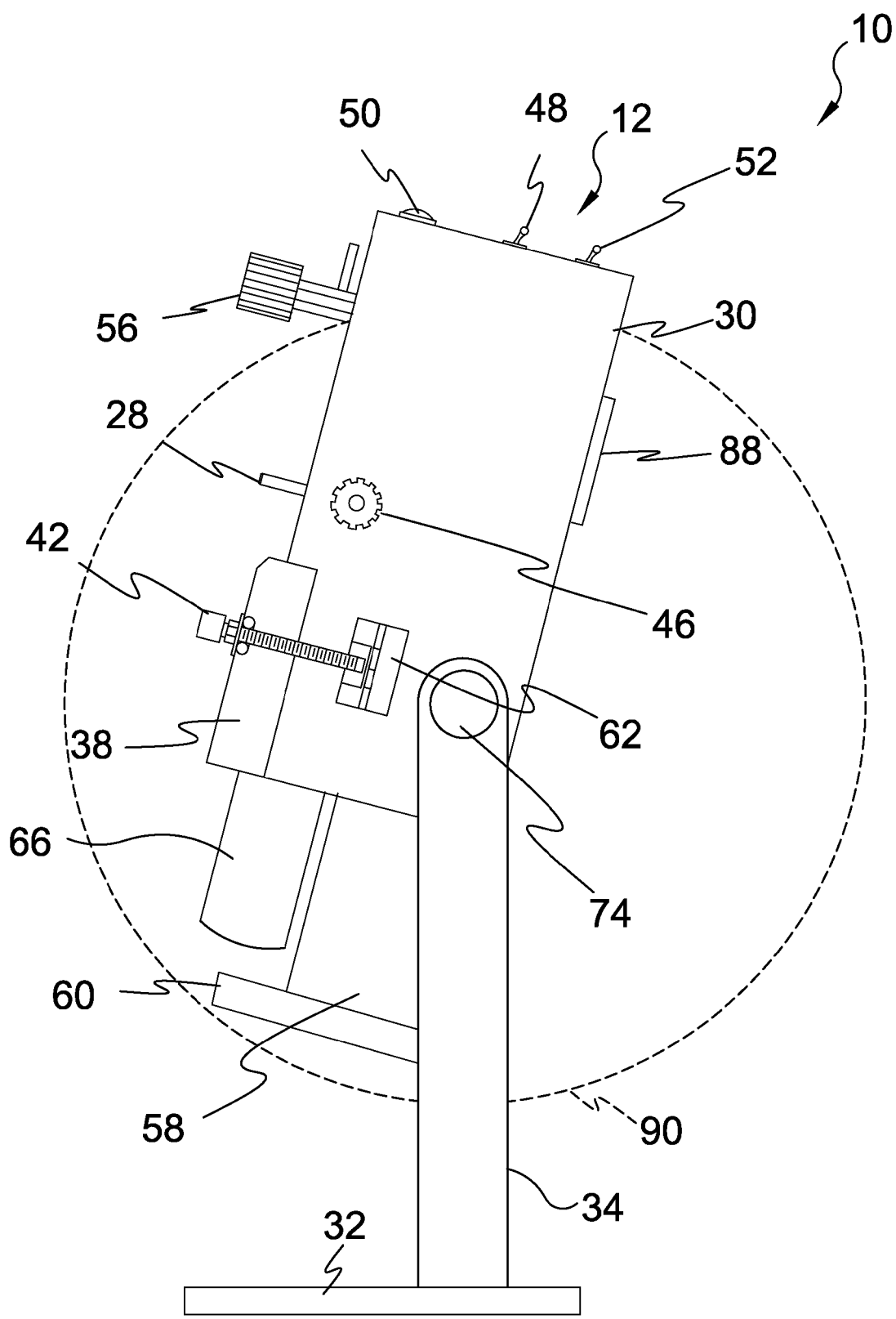
FIG. 10 is a side view of the present invention.

FIG. 10 is a side view of the dispenser 12 of the present invention 10. Shown is the present invention 10 with the dispenser housing 30 rotated on the rotating support 34 with the an aerosol can 66 loaded and the access door 38 closed and secured by the hinged 62 access door locking member 42. demonstrated in dashed line is the 360 degree rotation 90 capability of the housing 30. Once positioned, the housing 30 is locked at the selected angle with the rotation alignment locking knob 74. Fine targeting of the sighting laser 28 is achieved with the laser alignment locking knob 46. A timer 88 is provided to allow for user selected timed release of the contents of the aerosol can 66. Also shown is the relative positioning of the cam rod 56, the alignment test button 50, laser switch 48, cam motor switch 52, balancing weight 60, storage compartment 58 and the base 32.

Figure 11:
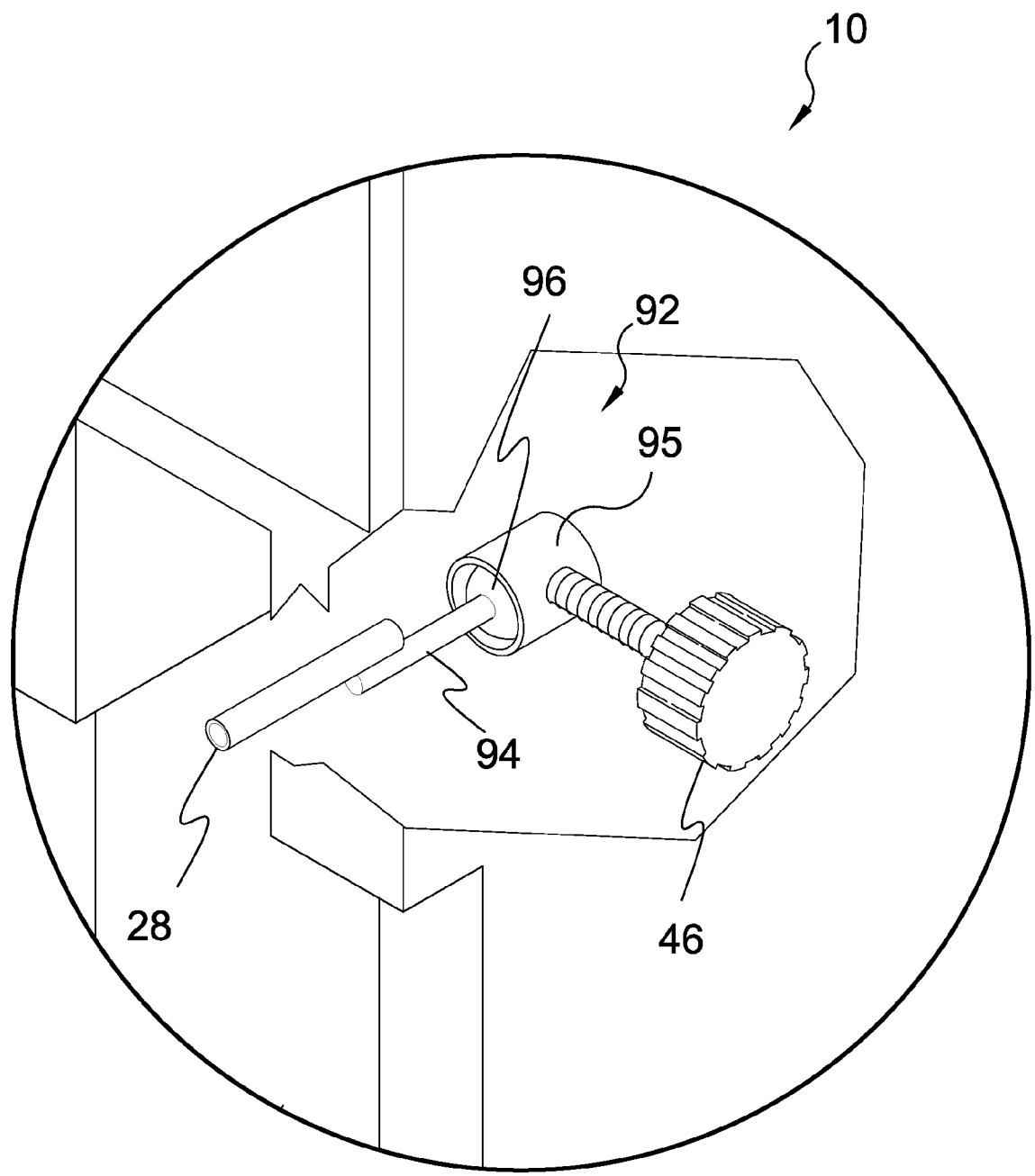
FIG. 11 is a detailed view of the present invention.

FIG. 11 is a detailed view of the present invention 10. Shown is the multi-axis laser adjustment assembly 92 having a sighting laser pointer 28 mounted to a positioning rod 94 that attaches to a rotative positioning ball 96 located within a holding hub 95. The threaded laser alignment locking knob 46 allows the user to lock the position of the laser beam when it has zeroed in on its target.

Figure 12:
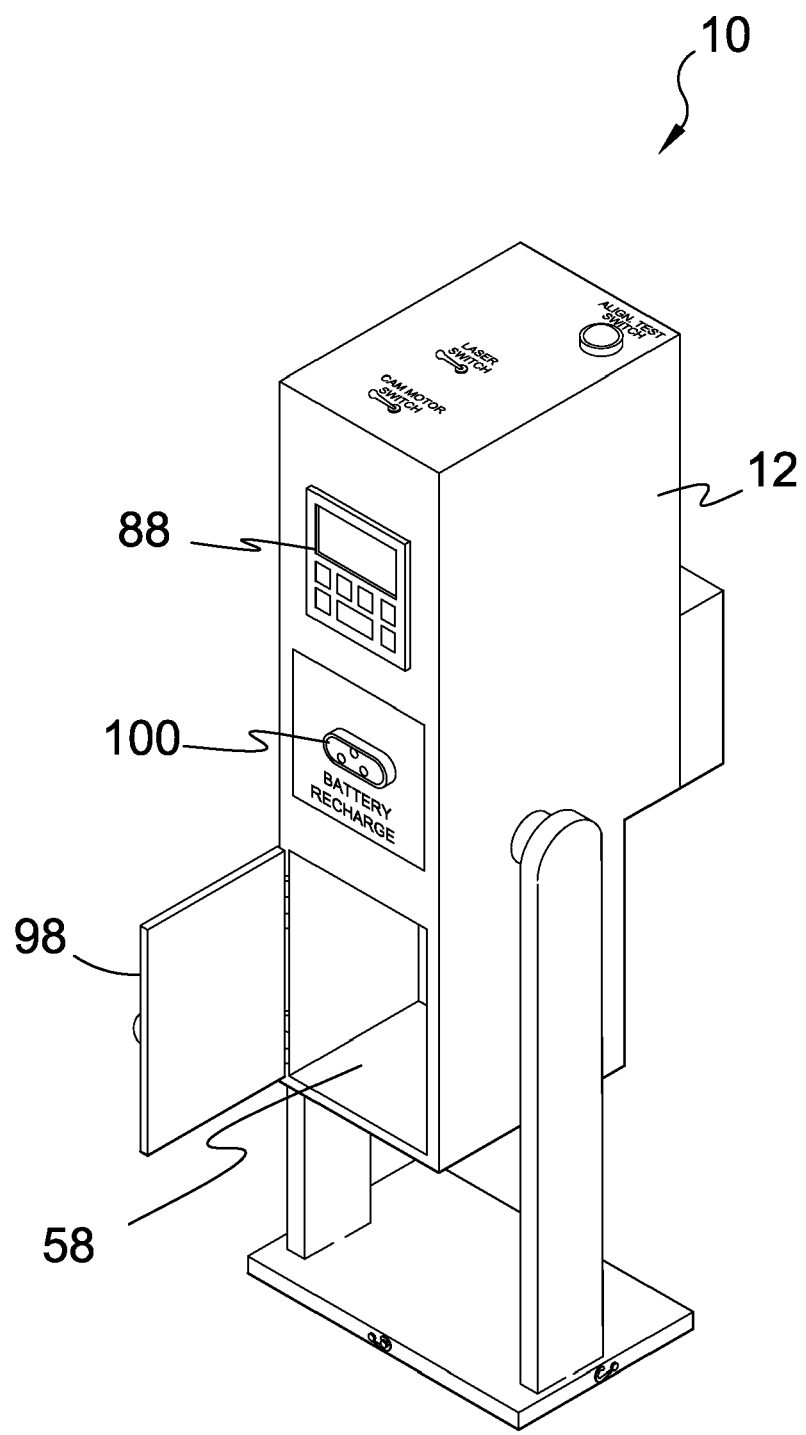
FIG. 12 is a rear view of the present invention

FIG. 12 is a rear view of the dispenser 12 of the present invention 10. Shown is a rear view of the dispenser 12 with the storage compartment door 98 open to reveal the storage compartment 58. The device also provides a timer 88 and rechargeable battery port 100.

Figure 13:
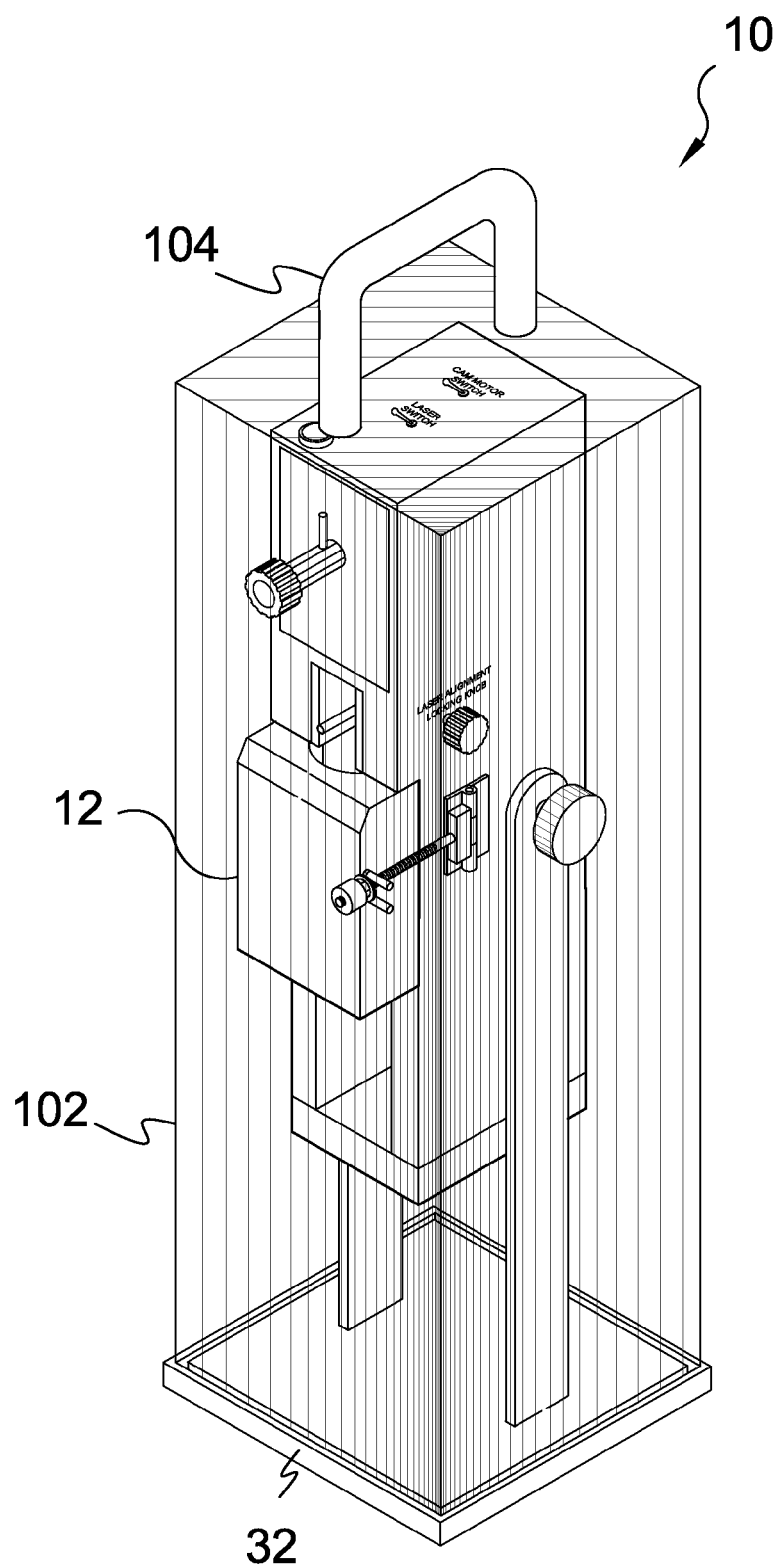
FIG. 13 is a perspective view of the present invention within its carrying case.

FIG. 13 is a perspective view of the dispenser 12 of the present invention 10 within its carrying case cover 102. The cover 102 has a handle 104 disposed on the top portion thereof and locks into the base 32.

Figure 14:
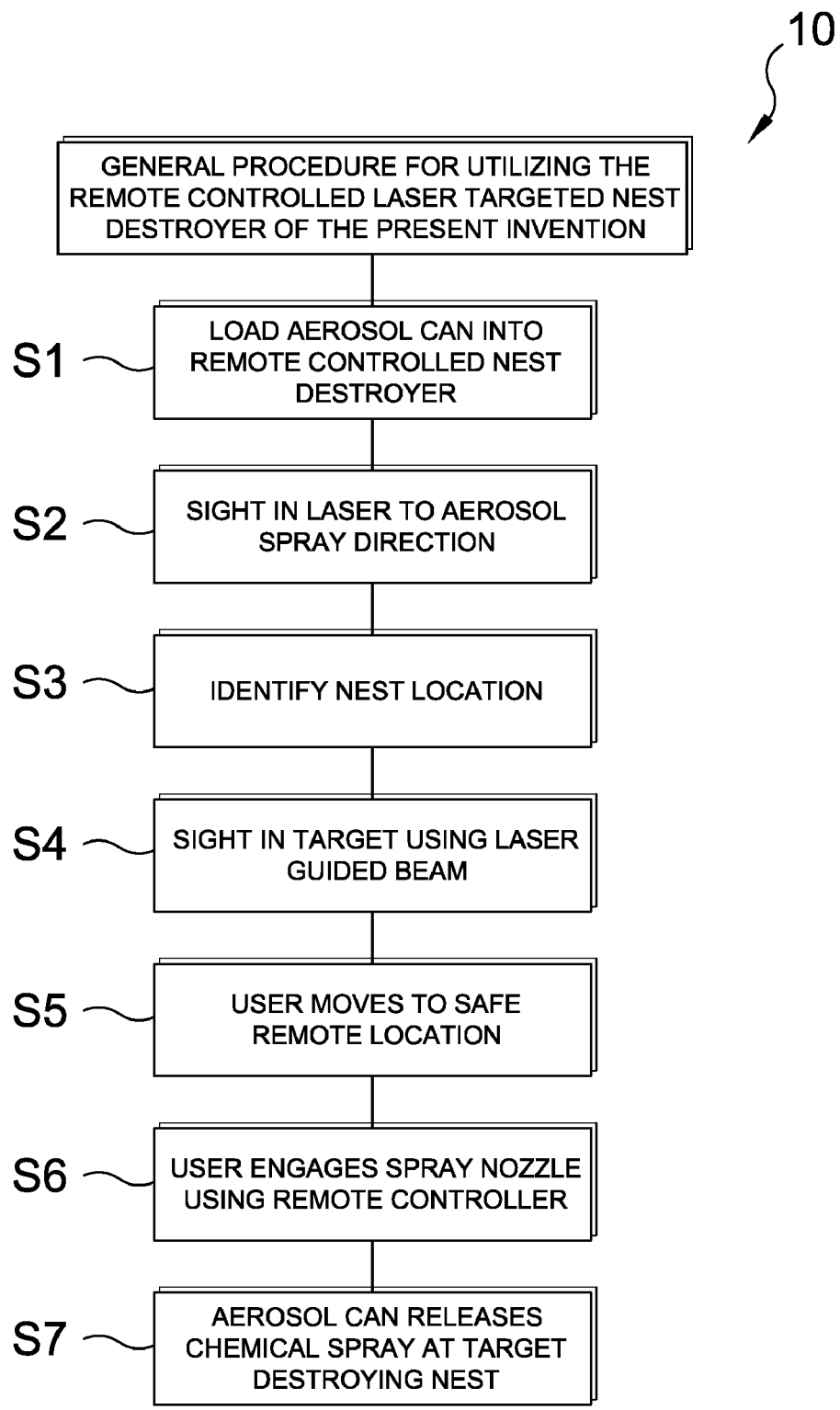
FIG. 14 is a flow chart for general operational procedures for the present invention.

FIG. 14 is a flow chart for general operational procedures for the present invention 10. Depicted is the order of operation for the remote controlled laser targeted nest destroyer of the present invention 10.

FIG. 15 is a flow chart for sighting the laser setup procedures for the present invention 10. Depicted below is the order of operation for sighting in the remote controlled laser targeted nest destroyer laser beam of the present invention 10 with the aerosol spray.

FIG. 16 is a flow chart for sighting target procedures for the present invention 10. Depicted is the order of operation for sighting in the target utilizing the remote controlled laser targeted nest destroyer of the present invention.

Figure 17:
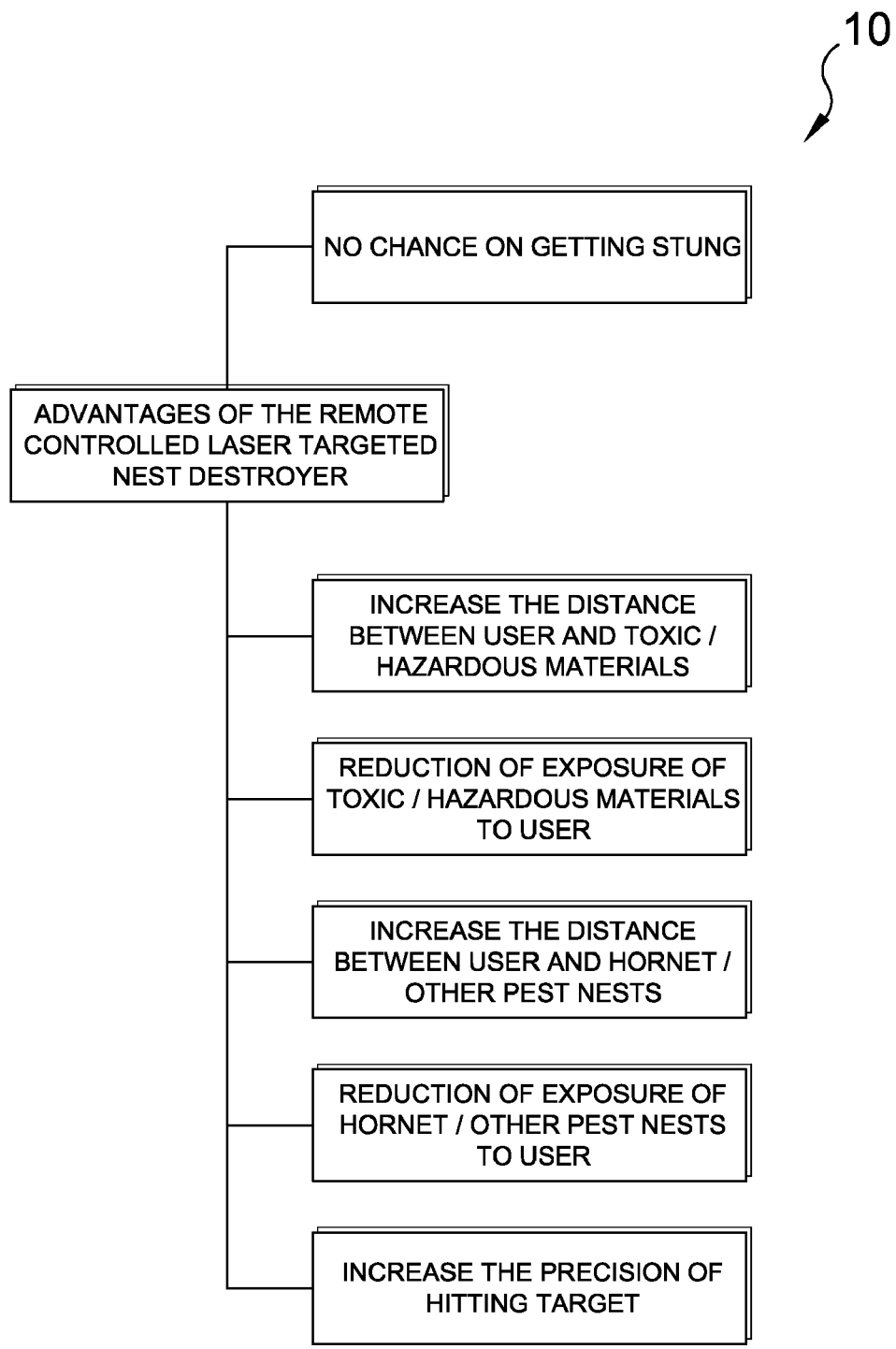
FIG. 17 is a block diagram for advantages of the present invention.

FIG. 17 is a block diagram for advantages of the present invention 10. Depicted are advantages of utilizing the remote controlled laser targeted nest destroyer of the present invention 10 in lieu of prior art.

Figure 18:
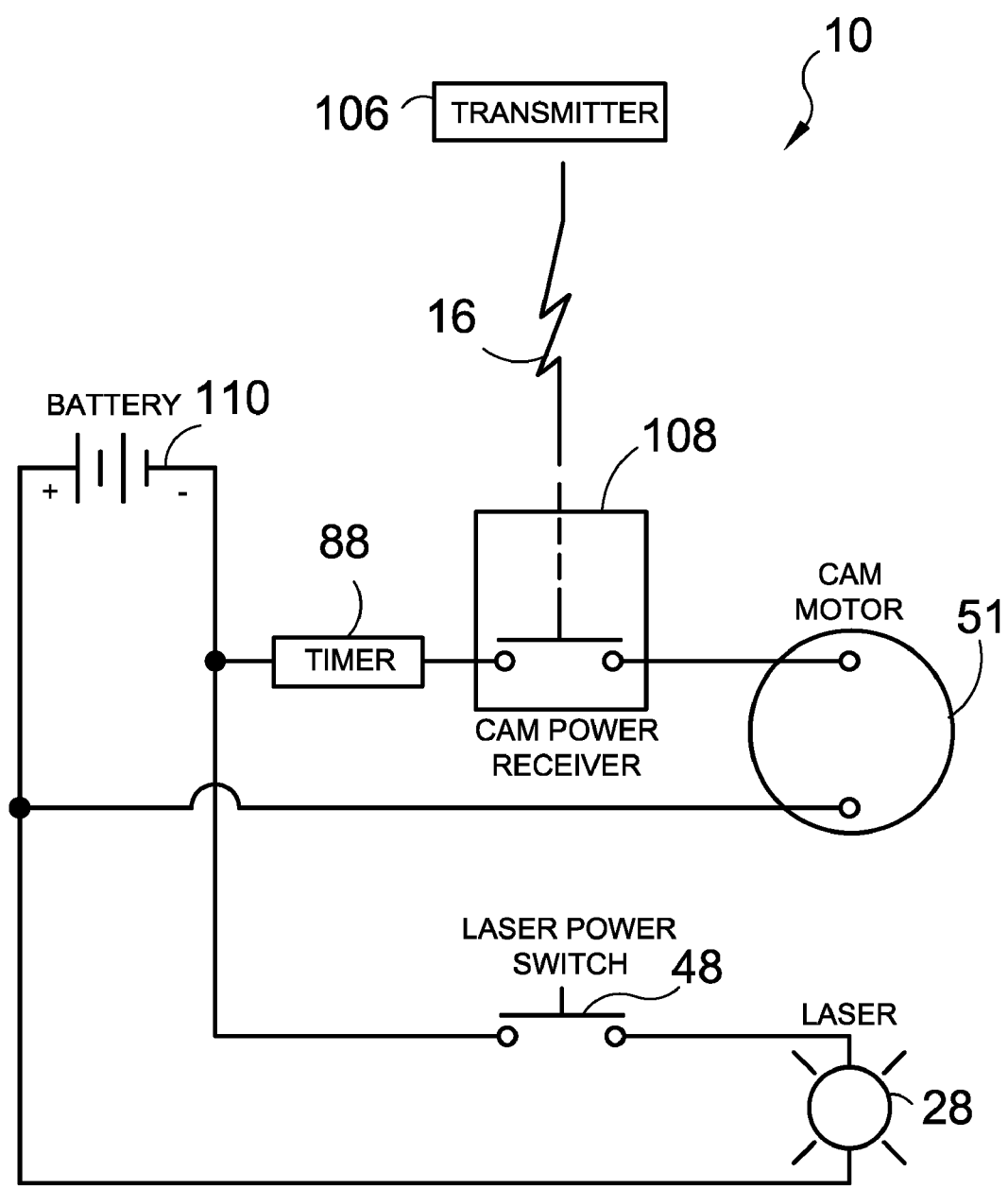
FIG. 18 is a schematic diagram of the present invention.

FIG. 18 is a schematic diagram of the present invention 10. Depicted below is the basic schematic diagram for the remote controlled laser targeted nest destroyer of the present invention 10. The cam to activate the spray can be obtained by either manual or automatic methods. Manually, the transmitter 106 sends a signal 16 to the cam power receiver 108 to activate the cam motor 51 remotely using R.C. or other wireless technology, else a timer 88 automatically activates the spray at an interval preset by the user for periodic discharging of either an insecticide or an air fragrance can. Power is supplied to the laser 28 through a laser power switch 48 from a rechargeable battery 110.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A remote operated insecticide and fragrance dispensing apparatus for delivering the contents of an aerosol can to a specified target in an accurate, controlled manner, said apparatus comprising:
   a) a housing having a cavity defining a receiving compartment for the aerosol can to be discharged;
   b) a base with at least one support rotatively retaining said housing thereon to enable the user to position said housing within a 360 degree axial rotation relative to said support;
   c) a laser pointer for sighting the target area to receive the discharge of said aerosol can contents;
   d) a multi-axis laser adjustment assembly to provide incremental adjustments when sighting said laser with said target;
   e) a cam assembly for actuating the discharge of said aerosol can, wherein the cam assembly comprises:
      i) a cam,
      ii) a cam motor to drive said cam,
      iii) a pivoting cam plate angularly disposed beneath said cam with the free end having an upward bias when in the static off position,
      iv) a microswitch disposed beneath said cam plate, and
      v) a push rod having a top portion having a magnetic tip adjacent to said microswitch and a bottom end oriented towards and proximal to the discharge button of said aerosol can; and
   f) remote means for actuating said cam assembly.

2. The remote operated insecticide and fragrance dispensing apparatus recited in claim 1, wherein said can receiving compartment includes a pivoting access door that is secured and released by a receiving compartment locking member hinged to said housing and having a threaded shaft that is received by a bifurcated latch integral with said access door.

3. The remote operated insecticide and fragrance dispensing apparatus recited in claim 2, wherein said aerosol can is retained in place in said receiving compartment with a plurality of magnets.

4. The remote operated insecticide and fragrance dispensing apparatus recited in claim 3, wherein said housing is rotated to a desired position on said rotating support and secured in the user selected position with a rotation alignment locking knob that has a threaded shaft that screws into a lock nut in said housing and is tightened to prevent the rotational displacement thereof.

5. The remote operated insecticide and fragrance dispensing apparatus recited in claim 1, wherein said multi-axis laser adjustment assembly comprises:
   a) a positioning rod in linear alignment with said laser pointer and engaged therewith;
   b) a rotative ball disposed within a holding hub; and
   c) a laser alignment locking knob threaded into said hub.

6. The remote operated insecticide and fragrance dispensing apparatus recited in claim 5, wherein said user adjusts said laser pointer until zeroed in on said target and secures the position by tightening said laser alignment locking knob.

7. The remote operated insecticide and fragrance dispensing apparatus recited in claim 1, wherein rotation of said cam applies a downward bias to said cam plate and contacts said microswitch and said magnetic end of said push rod thus depressing said discharge button on said can and releasing the contents therefrom to the target area.

8. The remote operated insecticide and fragrance dispensing apparatus recited in claim 7, wherein said cam assembly further comprises a cam rod and cam motor switch.

9. The remote operated insecticide and fragrance dispensing apparatus recited in claim 7, wherein said cam assembly further comprises an alignment test button for verifying alignment of said push rod with said discharge button.

10. The remote operated insecticide and fragrance dispensing apparatus recited in claim 9, wherein said cam motor and laser pointer are powered by a rechargeable battery that has a recharging port disposed in the rear of said housing.

11. The remote operated insecticide and fragrance dispensing apparatus recited in claim 1, wherein said remote actuation means comprises:
   a) a remote control unit having a transmitter to send a signal in response to the user's command; and
   b) a cam power receiver for receiving said signal from said transmitter.

12. The remote operated insecticide and fragrance dispensing apparatus recited in claim 1, wherein said remote actuation means is a user programmable timer that automatically activates spray discharge at preset intervals.

13. The remote operated insecticide and fragrance dispensing apparatus recited in claim 9, wherein said push rod is available in a plurality of sizes to accommodate the differentiation of various aerosol cans.

14. The remote operated insecticide and fragrance dispensing apparatus recited in claim 1, wherein said homing further comprises a storage compartment disposed at the rear of said housing for storage of aerosol cans and push rods.

15. The remote operated insecticide and fragrance dispensing apparatus recited in claim 1, wherein said housing includes a balancing weight disposed at the bottom portion thereof.

16. The remote operated insecticide and fragrance dispensing apparatus recited in claim 15, further including a carrying case having a handle member disposed on the top portion a bottom portion that locks into said base.

17. The remote operated insecticide and fragrance dispensing apparatus recited in claim 9, wherein said remote control operates to turn said cam and series of linkages in a manner whereby said pushrod is driven downwards to discharge the held aerosol can at an interval relative to said cams speed setting.

* * * * *